United States Patent [19]

Marconi

[11] Patent Number: 4,535,484

[45] Date of Patent: Aug. 20, 1985

[54] CARDIAC VALVULAR PROSTHESIS OF MECHANICAL TYPE PROVIDED WITH TWO FREELY MOVING LEAFLETS

[76] Inventor: Walter Marconi, Via A. Barilatti no. 72, 00144 Roma, Italy

[21] Appl. No.: 355,129

[22] Filed: Mar. 5, 1982

[30] Foreign Application Priority Data

Mar. 17, 1981 [IT] Italy .............................. 48040 A/81
Dec. 11, 1981 [IT] Italy .............................. 49893 A/81

[51] Int. Cl.³ .............................................. A61F 1/22
[52] U.S. Cl. .................................... 623/2; 137/512.1; 137/527
[58] Field of Search .................. 3/1.5; 137/512.1, 527, 137/527.8

[56] References Cited

U.S. PATENT DOCUMENTS

| | | | |
|---|---|---|---|
| 3,689,942 | 9/1972 | Rapp | 3/1.5 |
| 3,903,548 | 9/1975 | Nakib | 3/1.5 |
| 4,363,142 | 12/1982 | Meyer | 3/1.5 |
| 4,373,216 | 2/1983 | Klawitter | 3/1.5 |

*Primary Examiner*—Ronald L. Frinks
*Attorney, Agent, or Firm*—Hedman, Gibson, Costigan & Hoare

[57] ABSTRACT

Cardiac valvular prosthesis of mechanical type consisting of a sewing ring welded to a housing orifice where, in the absence of pins or hinges, two leaflets, preferably provided with a slight curvature, are free of moving with both rotation and translation movement. This is achieved through suitable metal structures, able both to permit the correct opening and closing of the leaflets (i.e. to act as rotation fulcrum) and to guarantee the guidance and the right positioning of the leaflets (i.e. to exert a constraint).

The "rotation fulcrum" and the "constraint" structures can be separated and independent, or can form part of one structure devoid of discontinuity; this latter case is shown in FIGS. 3 and 4 of the drawing. The leaflet thickness can also not be uniform, as well as the profiles of the two sides of each leaflet can be different.

10 Claims, 25 Drawing Figures

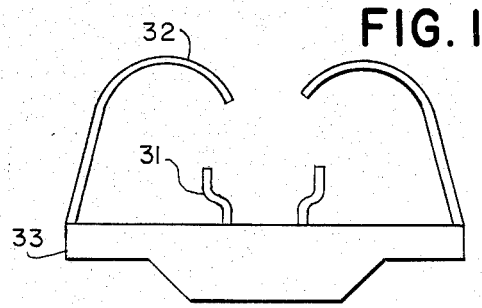
FIG. 1
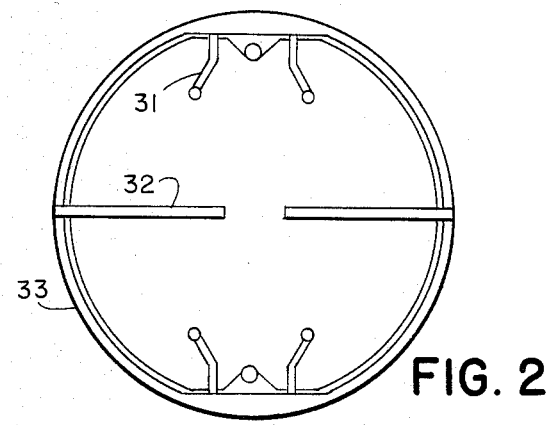
FIG. 2
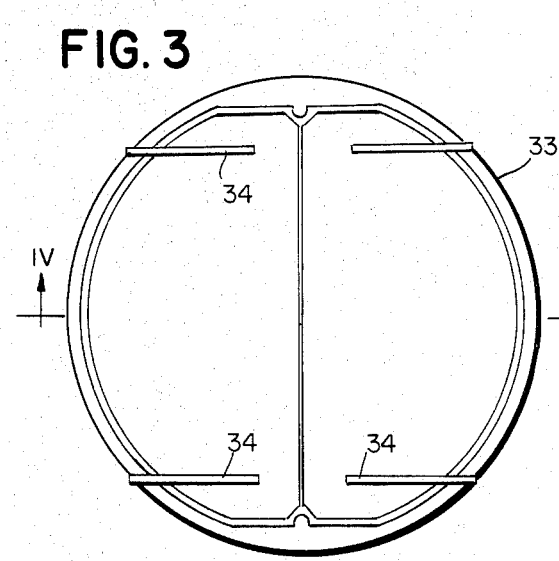
FIG. 3
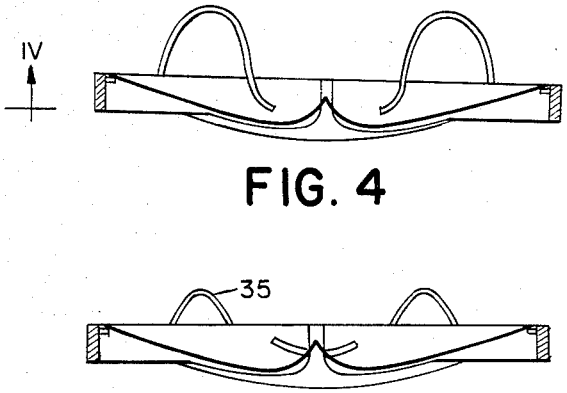
FIG. 4
FIG. 6
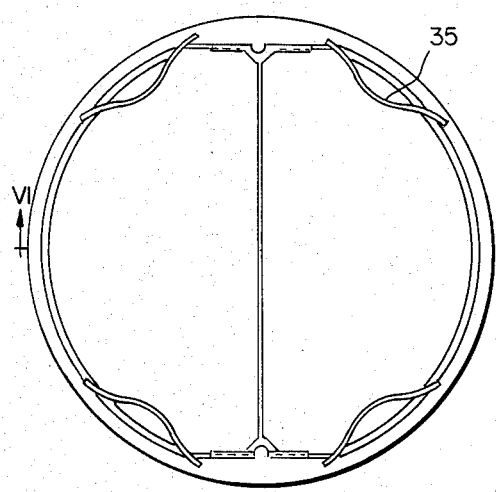
FIG. 5
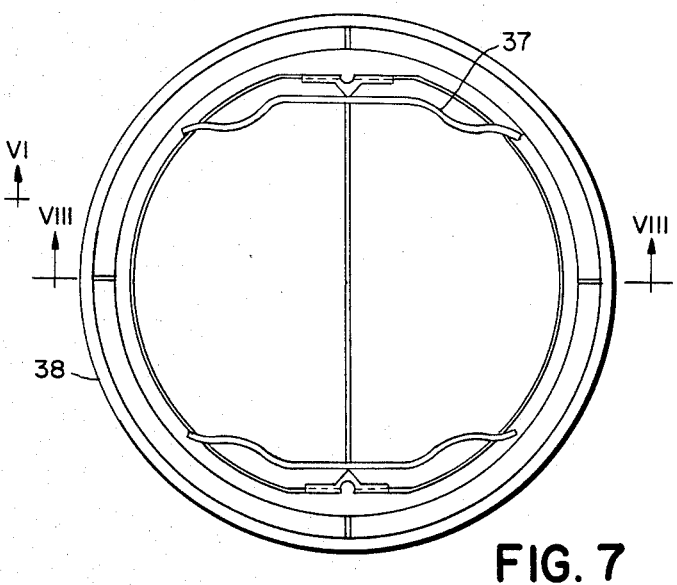
FIG. 7

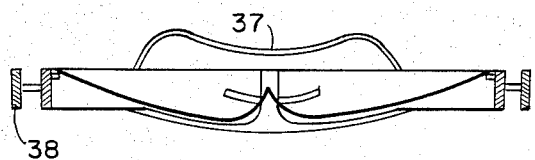
FIG. 8
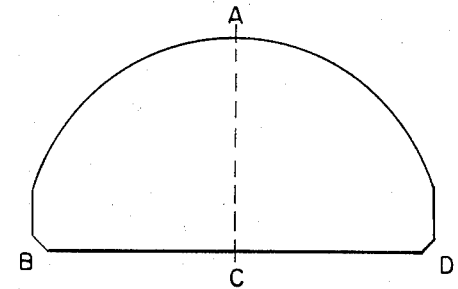
FIG. 9
FIG. 10
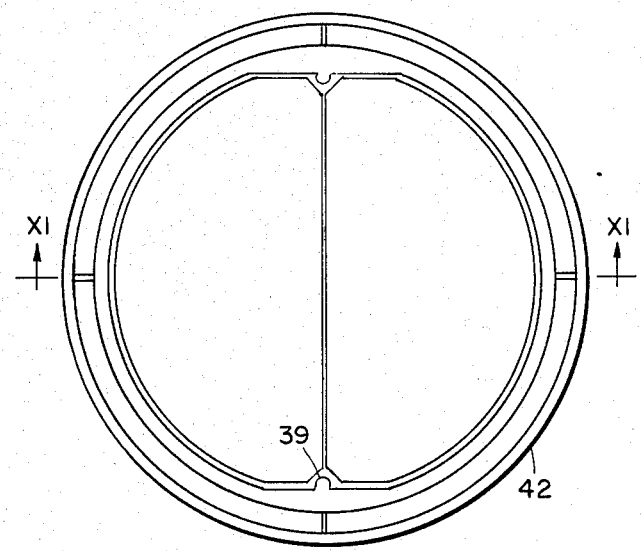
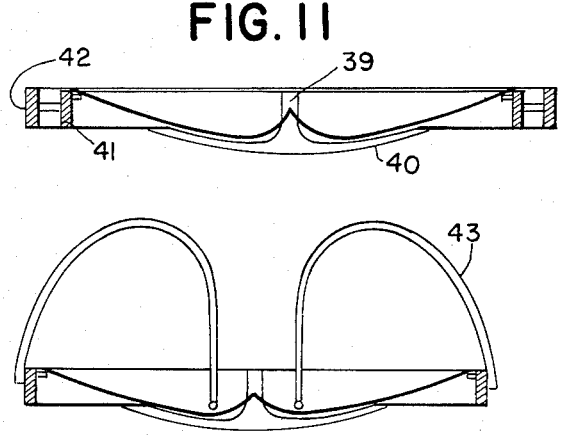
FIG. 11
FIG. 13
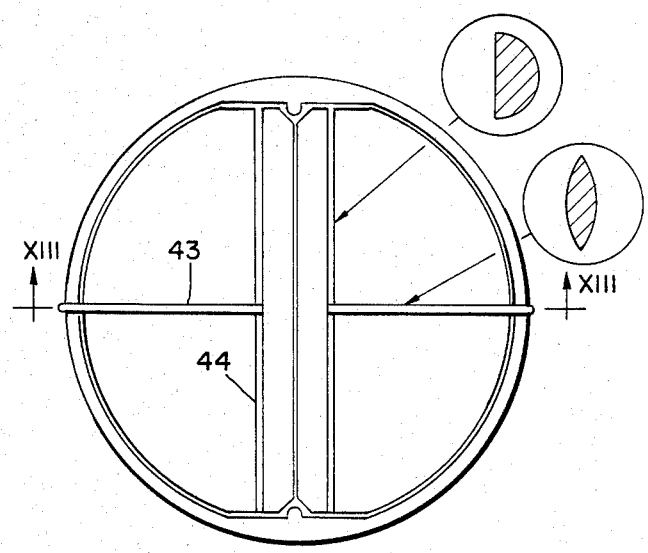
FIG. 12
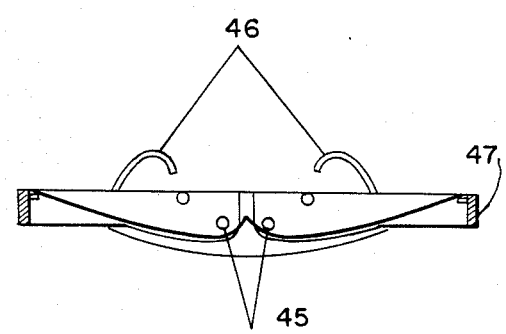
FIG. 14 ically inert, has not to damage the blood constituents, must possess a high abrasion resistance, and above all must not give rise to formation and growth of thrombi. The introduction of the pyrolytic carbon as a material for the construction of the occluder and, in some types of valve, also as a coating of the metallic parts of the valve, has been an important improvement, even if a permanent anticoagulant therapy is nevertheless generally necessary for bearers of any type of mechanical cardiac prothesis.
CARDIAC VALVULAR PROSTHESIS OF MECHANICAL TYPE PROVIDED WITH TWO FREELY MOVING LEAFLETS

DESCRIPTION

This invention relates to an artificial cardiac valve of mechanical type, provided with two leaflets mobile with a rotation-translation movement.

The cardiac valvular substitution, necessary in a large number of cases of congenital or acquired malformations, after twenty years since the first surgical intervention of this type and in spite of the great progress made both in the surgical techniques and in the valve design, is still a partially unsolved problem.

If we don't consider the "homograft", i.e. the transplantation of a valve obtained from a human cadaver, the main classes of prosthetic valves to date employed are the following two:

(1) Rigid mechanical prostheses
(2) Valves by biological non linving tissue, such as the "heterografts", i.e. the valves obtained from porcine cadaver, as well as valves made by tissues of good flexibility and mechanical resistance, like "dura mater" and "fascia lata".

The biological valves, endowed with a better biocompatibility and not requiring generally an anticoagulant therapy, meet a severe limitation in their use imposed by their scarse durability: after few years, and even before if the valve recipients are young people, a degeneration of the prosthesis takes place, with massive calcifications, cusps perforation and extended histological modifications, with consequent loss of the necessary functionality.

Mechanical prostheses have so to be considered the elective therapy when the life expectancy of the recipient must be considered long, i.e. to date in most cases.

A mechanical valvular prosthesis is generally consisting of:

(a) a rigid circular seat (flow orifice or valve housing), welded to an external ring covered by a fabric, in order to permit its insertion into the patient, through a suture
(b) the flow orifice occluder, which can be a disc, a ball, or some leaflets
(c) a structure aiming at guiding and limiting the motion of the occluder such as a cage, wire structures or hinges.

A good prosthesis must possess many requirements, concerning both fabrication material and valve design.

The material must be chemically inert, has not to damage the blood constituents, must possess a high abrasion resistance, and above all must not give rise to formation and growth of thrombi. The introduction of the pyrolytic carbon as a material for the construction of the occluder and, in some types of valve, also as a coating of the metallic parts of the valve, has been an important improvement, even if a permanent anticoagulant therapy is nevertheless generally necessary for bearers of any type of mechanical cardiac prothesis.

Even more numerous are the requirements for the valve design, that must guarantee the maximum possible orifice area consistently with the dimensions of the anatomical annulus where it has to be inserted, in order to obtain an optimization between highest possible cardiac output and lowest pressure gradient through the orifice.

Other necessary requirements are: a fast opening; a fast and effective closure, in order to guarantee the lowest regurgitation of the blood flow; to guarantee a central and laminar blood flow, with minimal flow resistance. This latter feature, very important also in order to avoid thrombus formation, is suitably achieved by using the socalled "low profile" occluders, like a tilting disc or two leaflets, for which the obstruction section of the valvular housing, during the opening phase, is very small.

Out of the very many types of cardiac valves to date tried (more than 40), only few ones are presently still in use, and they fulfill, at least partially, the abovementioned requirements. Out of these, we can mention the "ball and cage" valve by Starr and the Smeloff "double cage" valve, that have however the disadvantage of having no "low profile", with a consequent considerable disturbance (and no centrality) of the hematic flow lines across the valve.

An improvement, from this point of view, is represented by the disk valves, such as the "tilting disk" valve by Biörk, or the "pivoting disk" valve by Lillehei. In these cases, however, it was noticed that the disc, in the opening position, partitions the valve orifice into two compartments of different area, with different flow and flow rate across them. As a consequence, formation of thrombi over the disc, in the surface zone where the flow rate is lower, was noticed (Fernandez J. et al., Chest, 70, 12 (1976) Moreno-Cabral R. J. et al., J. Thoracic Cardiovascular Surgery 75, 321, (1978)). Better results, from the hemodynamic point of view, were obtained by valves such as the "Edimburgh valve" by Mc Leod, or the "St. Jude Medical valve", where the occluder, respectively consisting of a disc or of two semicircular flat leaves, puts itself, in the position of maximum opening, almost parallel to the hematic flow lines.

A remarkable disadvantage of this type of valves is the presence of pins or hinges, necessary in order to permit the fast rotation of the occluder. These pins and hinges proved to be dangerous starting points for the formation of clots ((L. Nunez et al., Annals Thoracic Surgery, 29, No. 6, 567 (1980)).

From the previously described state of the art it turns out that a valve of new type, possessing a low profile occluder (able to guarantee flow laminarity and maximum orifice area), and requiring no pins, hinges, joints or similar to ensure its correct motion, would represent a real progress in the exploitation of prosthetic cardiac valves.

The present invention precisely relates to a new cardiac valvular prosthesis, of mechanical type, consisting of:

(1) a circular orifice where lay two leaves, preferably provided with a slight curvature
(2) a system of strong metallic elements aiming both at making the leaflet rotate (under the action of the blood flow) up to the position of maximum opening, and at preventing the leaflet from coming out of the valve housing, in any position and time.

This structure of metallic elements, for example wire, generally consists of a part close to the leaflet concavity (if the leaflet has a curvature) and acting as rotation fulcrum, and of one or more arches or arch segments (per each leaflet) having the function of guaranteeing the guidance and the correct positioning of the leaflet (constraint structure). From the viewpoint of the fabrication modalities, these structures can be separated and independent, as well as they can form part of one structure devoid of discontinuity. The "rotation structure", i.e. that part of the system of metallic elements having the function of compelling the leaflets to rotate, may consist of short metal filaments, often provided with a slight curvature, and welded to the flow orifice of the valve.

The rotation structure can also be carried out by means of a simple pawl, placed just above the leaflet, in such a position that the leaflet is compelled to a rotation-translation movement. A second pawl having a double function of guidance and stop, can be placed in an upper position (see FIG. No. 14). The "rotation fulcrum" structure can also be made out of the body itself of the flow orifice of the valve, and consist of a gage or thickness made out in the middle of the valve, above the grooves supporting the leaflets and letting them slip, as illustrated in FIG. No. 16.

The constraint structure can as well be realized, rather than by means of one or more arches or arch segments, by means of short wire welded over the housing ring of the valve, to form four or alternatively two curved eyelets, able to prevent the leaflet from getting out, and able to achieve this with minimum flow disturbance (see FIGS. 5–8).

In the opening phase, the leaflets reach quickly a position almost perpendicular to the flow orifice of the valve; this gives rise to two sufficiently broad flow side-sections, which form, together with the central flow section, a system of three openings having a flow section broad enough to guarantee a good flow laminarity.

The rotation-translation movement of the leaflets takes place through slipping of the extremities of the basis edge of the leaflet along a generally curved groove, made out in the inside of the housing ring of the valve, in its central position (this detail appears in almost all figures and particularly FIG. 11 ref. No. 40, FIG. 21 ref. No. 53 and FIG. 23 ref. No. 54).

The valve leaflets, besides semicircular, can be semi-ellipsoidal, and in this case they show a distance between the apex and the base edge of the leaflet that is higher than the half-length of the base edge (see for a better understanding FIG. 9, where the half-length of the base edge BC is shown shorter than the distance AC between the base edge BD and the apex A of the leaflet).

This particular geometry makes easier the free slipping of the edge of the leaflet along the grooves of the housing ring during the opening and closing phases.

In order to make the movement easier and quicker, the leaflets can be provided with a suitable curvature, whose concavity is turned towards the rotation fulcrum of the leaflet (see FIGS. 6 and 8, 11, 13, 14 and 16). The curvature is often located only close to the base edge of the leaflet, whose profile pursues then straight on.

The leaflet thickness can be uniform, with both sides (whenever curved) having the same curvature radius, or they can have different curvature radii. The leaflet can so have an uniformly growing thickness, as well as can be thicker only in some points, as in the middle or near the edges.

Alternatively, the leaflet can have the side leaning on the slipping grooves provided with the usual convex profile, whereas the side turned towards the rotation fulcra, instead of being concave, consists of two plane surfaces forming an angle between each other (see FIG. No. 18). A further improvement of the hemodynamic flow can be achieved by realizing each profile of the valve side by two plane surfaces forming an angle between each other, as shown in FIG. 20.

In another modality of realization of the leaflets, in order to make easier in the phases both of opening and closing of the leaflet its movement along the slipping grooves, the side edge of the leaflet, (or at least the part of the edge beeing in contact with the groove) has a rounded profile, whose convexity is turned towards the groove. This appears in the FIG. No. 24', where the Sec. BB shows the abovementioned leaflet section. Since the leaflet structure influences that of the groove, when leaflets having a rounded profile are employed, the section of the groove will also have to be rounded, with a curvature similar to that of the edge of the leaflet, and concavity turned towards it, as shown in the FIG. No. 10b', where the Sec. AA is the groove section. Similarlly, when the leaflet sides consist of plane surfaces forming an angle between each other, also the profile of the groove on which the leaflet slips can be straight instead of curved (see FIG. No. 9b).

In order to decrease even more the opening and closing times of the valve, the slipping grooves (both curved and straight) can have an ascending profile, and their Z-coordinate with respect to the basis plane of the valve can be higher at the end of the groove (i.e. towards the apex of the leaflet) than at the origin point of the groove (i.e. in the middle of the housing ring of the valve). This is shown, respectively for a straight or a curved groove, in FIG. 21 (ref. No. 53) and FIG. 23 (ref. No. 54).

In order to prevent faulty positioning, or even coming out of the leaflets, the flow orifice of the valve can be provided, in its middle, with edges in relief which get in touch with the extremities of the edges of the leaflets in their closure position.

These edges in relief are perpendicular to the flow orifice, are located in the internal part of the flow orifice, and extend from the beginning of the slipping grooves up to the upper rim of the flow orifice as shown in FIG. 11, ref. No. 39).

In the closure position, the leaflets rely on the inside of the valve flow orifice, generally in a slightly inclined position.

The section of the metallic elements forming both the rotation and the constraint structures can be different from the circular one; rectangular, semi-circular, drop-shaped, or wedge-shaped sections can effectually contribute to improve the hemodynamic flow through the valve.

The cardiac valvular prosthesis which I have invented is illustrated diagramatically in the accompanying drawings.

FIG. 1 is a side elevation of a valve where 31 is the rotation fulcrum of the leaflet (not represented in the drawing for sake of simplicity), 32 represents the guide and constraint structure of the valve, 33 represents the flow orifice (valve housing).

FIG. 2 is a plan view of the configuration illustrated in FIG. 1.

FIG. 3 is a side elecation of another realization where the rotation fulcrum of the valve and the guide and positioning structure are realized by means of one metallic element.

FIG. 4 is a section taken on line IV—IV of FIG. 3.

Figure 15:
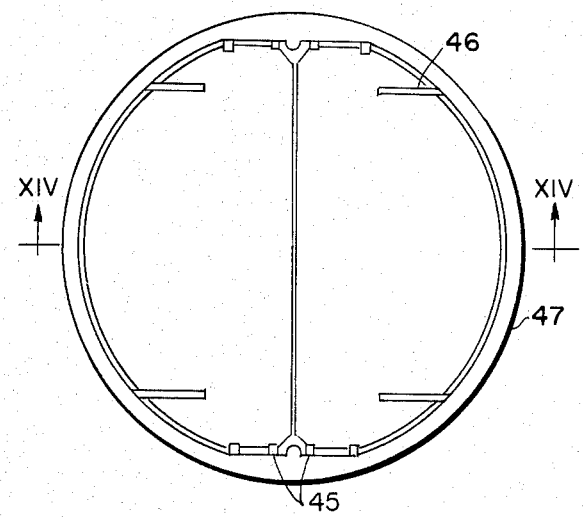

FIGS. 5 and 6 illustrate a modification where the constraint structure 35 consists of short wire welded over the housing ring of the valve to form four curved eyelets, whereas in FIGS. 7 and 8 the constraint structure 27 consists of wire forming only two curved eyelets.

In FIGS. 7 and 8 it is also shown (ref. No. 8), the sewing ring of the valve.

FIG. 9 shows a semi-ellipsoidal leaflet where the half-length of the base edge BC is shorter than the segment AC.

FIGS. 10 and 11 show the edges in relief (ref. No. 39), located in the internal part of the flow orifice and perpendicular to the housing plane of the valve (i.e. parallel to the flow lines across the orifice).

In FIGS. 10 and 11 it is also indicated, with the ref. No. 42, the sewing ring of the valve.

FIG. 11 shows a typical realization of the slipping groove 40, inside the ring 41.

FIGS. 12 and 13 show a valve where rotation fulcrum and constraint structures are realized by means of one metallic structure, in a continuous way; moreover, in this realization, the section of the constraint structure 43 is "wedge-like", whereas the section of the rotation structure 2 is semi-circular.

FIGS. 14 and 15 show the two projections of a realization where the rotation fulcra of the valve are formed by the pawls 45; 46 represents the constraint structures of the valve, 47 represents the flow orifice ring.

Figure 16:
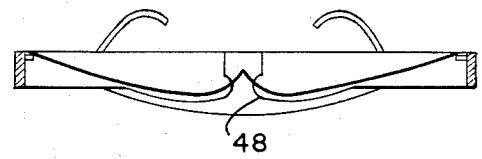
Figure 17:
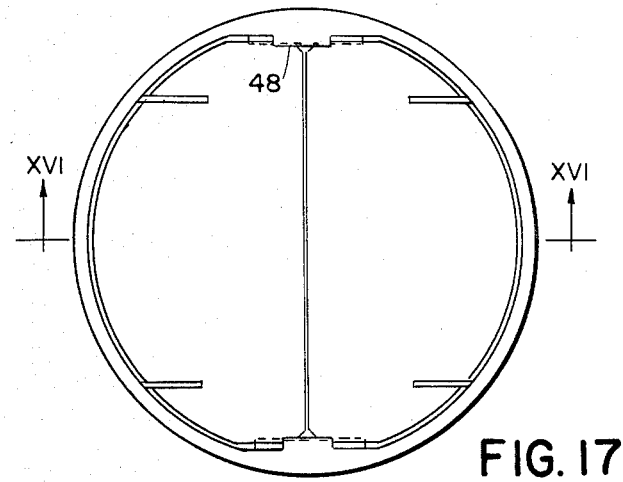

FIGS. 16 and 17 show the two projections of a valve where the rotation fulcrum structure 48 is made out of the body itself of the flow orifice ring of the valve.

Figure 18:
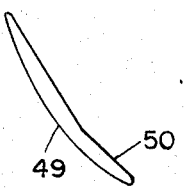
Figure 19:
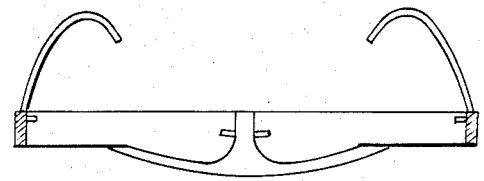

FIGS. 18 and 19 show a realization where the leaflet sides consist of a convex surface (side 49) and of two plane surfaces forming an angle between each other (side with ref. No. 50).

Figure 20:
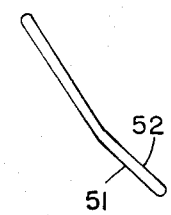
Figure 21:
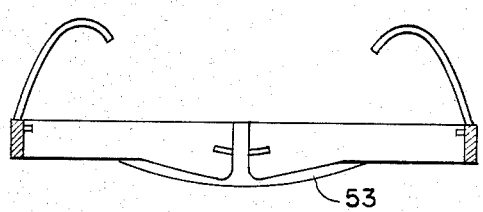
Figure 22:
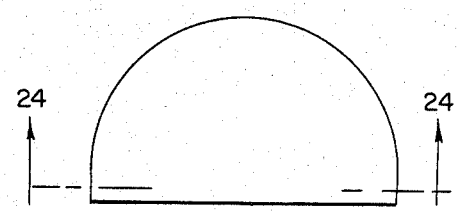

In FIGS. 20 and 21 each of the sides (51 and 52) of the leaflet consists of two plane surfaces forming an angle between each other. For this reason, the profile of the slipping groove 53 is straight instead of curved.

Figure 23:
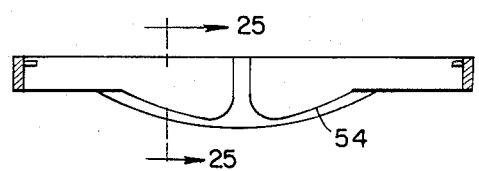
Figure 24:
Figure 25:
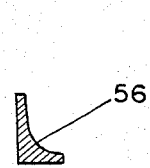

FIGS. 22–25 show a valve where the side edge 55 of the leaflet has a rounded profile (FIGS. 22 and 24), whose convexity is turned towards the valve slipping groove 54, whose section 56 is curved, with the concavity turned towards the edge of the leaflet (FIGS. 23 and 25).

Furthermore, FIGS. 21 and 23 also illustrate slipping grooves 53 and 54 (both straight and curved) having an ascending profile, with a Z-coordinate (with respect to the basis plane of the valve) higher at the end of the groove than in the middle of the valve.

What I claim is:

1. A mechanical cardiac valve prosthesis comprising:
   (a) a housing ring forming a flow orifice;
   (b) a sewing ring on the external surface of said housing ring;
   (c) a pair of leaflets with edges free of projections placed in said housing, each leaflet guided by a rotation fulcrum structure and by a constraint structure on said housing ring so that it moves freely from an opened to a closed position;
   (d) said housing ring having on its internal surface curved grooves that engage the edges of each of said leaflets and imparts mixed rotation and translational movement to said leaflets as they move from said open to said closed position.

2. A mechanical cardiac valve prosthesis as defined in claim 1 wherein the rotation fulcrum consists of two pawls on the inside of said housing ring that are placed above the leaflet.

3. A mechanical cardiac valve prosthesis as defined in claim 1 wherein the constraint for the leaflets at the full open position is a segment of a metallic arch on said housing ring.

4. A mechanical cardiac valve prosthesis as defined in claim 3 wherein said constraint for the leaflets comprises short wire segments welded to said housing ring to form four curved eyelets.

5. A mechanical cardiac valve as defined in claim 1 wherein each leaflet has a semi-circular configuration.

6. A mechanical cardiac valve as defined in claim 1 wherein the leaflets have a semi-ellipsoidal configuration.

7. A mechanical cardiac valve as defined in claim 1 wherein the thickness of each leaflet is not uniform.

8. A mechanical cardiac valve as defined in claim 1 wherein the grooves are centrally located on the inside of said housing ring.

9. A mechanical cardiac valve as defined in claim 1 wherein the edges of said leaflets that contact the grooves have a rounded profile.

10. A mechanical cardiac valve as defined in claim 1 wherein the grooves have an ascending profile with respect to the base plane of the valve in order to decrease the opening and closing times for the valve.

* * * * *